United States Patent
Wong et al.

(10) Patent No.: US 7,967,604 B2
(45) Date of Patent: Jun. 28, 2011

(54) HEATED MOUTHPIECE

(75) Inventors: Davy Wong, Fotan (HK); David Colangelo, Tampa, FL (US); Jim Wetzel, Tampa, FL (US)

(73) Assignee: Creative Sourcing & Development Inc., Tampa, FL (US)

( * ) Notice: Subject to any disclaimer, the term of this patent is extended or adjusted under 35 U.S.C. 154(b) by 459 days.

(21) Appl. No.: 11/774,695

(22) Filed: Jul. 9, 2007

(65) Prior Publication Data

US 2009/0017417 A1  Jan. 15, 2009

(51) Int. Cl.
- *A61C 3/00* (2006.01)
- *A61C 5/14* (2006.01)
- *A61F 7/00* (2006.01)

(52) U.S. Cl. .............................. 433/32; 128/862; 607/96

(58) Field of Classification Search .................. 433/215, 433/32, 37, 80; 264/16, 17, 19, 222; 128/859, 128/860, 861; 424/435

See application file for complete search history.

(56) References Cited

U.S. PATENT DOCUMENTS

| | | | | |
|---|---|---|---|---|
| 4,919,245 A | * | 4/1990 | Braden | 165/10 |
| 4,944,947 A | * | 7/1990 | Newman | 424/435 |
| 5,771,789 A | * | 6/1998 | Davis | 99/468 |
| 6,364,665 B1 | | 4/2002 | Trettenero | |
| 6,382,979 B2 | * | 5/2002 | Lindquist | 433/215 |
| D539,429 S | | 3/2007 | Wong | |
| 2002/0172919 A1 | * | 11/2002 | Zavitsanos et al. | 433/32 |
| 2004/0101803 A1 | * | 5/2004 | Tucker et al. | 433/38 |
| 2005/0043655 A1 | * | 2/2005 | Schenck | 601/15 |
| 2006/0019214 A1 | * | 1/2006 | Lawrence et al. | 433/29 |

* cited by examiner

*Primary Examiner* — Todd E Manahan
*Assistant Examiner* — Yogesh Patel
(74) *Attorney, Agent, or Firm* — Larson & Larson, P.A.; Frank Liebenow; Justin Miller

(57) ABSTRACT

An application for a heated mouthpiece includes a mouthpiece section for insertion into the mouth of a user and a heat retention mass connected to the mouthpiece section and in thermal contact with the mouthpiece section whereby external heat provided to the heat retention mass before insertion into the mouth is partially retained by the heat retention mass and conducts to the mouthpiece section while the mouthpiece section is in use within the mouth.

10 Claims, 2 Drawing Sheets

HEATED MOUTHPIECE

FIELD OF THE INVENTION

This invention relates to the field of mouthpieces and more particularly to a mouthpiece that is heated and retains heat in order to activate a chemical substance placed on it.

BACKGROUND OF THE INVENTION

Oral devices known as mouthpieces are known in the industry for uses such as protecting the teeth, gums and bones during sporting events. Similar devices are known for performing various functions on the teeth such as whitening the teeth or taking impressions. Impressions are often taken before being fitted for braces, dentures, crowns, bridges, etc.

One such mouthpiece is described in U.S. Pat. No. D539,429 to Wong, which is hereby incorporated by reference. This design patent shows the ornamental layout of one such mouthpiece.

Another mouthpiece is described in U.S. Pat. Application No. 2001/0038998 to Lindquist. This application describes some of the reasons for heating a mouthpiece and includes a heated mouthpiece, but the heated mouthpiece of this application uses electric current or circulation of a heated liquid to perform the heating. Furthermore, even if such mouthpiece were heated by an external source such as a microwave oven, there is no mass within the mouthpiece that would absorb the heat and slowly release the heat to the rest of the mouthpiece.

Certain oral chemical compositions either require heat to work correctly or work better when heat is applied. For example, the action of dental bleaching agents or whiteners is known to accelerate when heated to a temperature greater than 105° F. The mouthpieces of the prior art do not provide for heating the chemical compounds used upon them, and do not provide for sustaining the heat over a useful length of time.

What is needed is a mouthpiece that will accept heat from an external source and transfer that heat to a substance disposed on the surface of the mouthpiece that contacts the user's teeth.

SUMMARY OF THE INVENTION

In one embodiment, a heated mouthpiece is disclosed including a mouthpiece section for insertion into the mouth and a heat retention mass connected to the mouthpiece section that is in thermal contact with the mouthpiece section whereby external heat provided to the heat retention mass conducts to the mouthpiece section while the mouthpiece section is within the mouth.

In another embodiment, a method of using a heated mouthpiece is disclosed including providing a heated mouthpiece, the heated mouthpiece has a mouthpiece section for insertion into the mouth. The mouthpiece section includes an upper trough for surrounding the upper teeth and a lower trough for surrounding the lower teeth. Connected to the mouthpiece section is a heat retention mass that is in thermal contact with the mouthpiece section whereby heat provided from the heat retention mass conducts to the mouthpiece section while the mouthpiece section is within the mouth. The method continues with heating the heat retention mass the placing an oral compound in the upper trough and placing an oral compound in the lower trough. Next, the mouthpiece section is inserted into the mouth with the upper teeth in the upper trough and the lower teeth in the lower trough whereas heat from the heat retention mass will transfer to the mouthpiece section and thereby to the oral compound, heating the oral compound.

In another embodiment, a heated mouthpiece is disclosed including a mouthpiece section for insertion into the mouth and a device for retaining heat connected to the mouthpiece section and in thermal contact with the mouthpiece section whereby external heat provided to the device for retaining heat conducts to the mouthpiece section while the mouthpiece section is within the mouth.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION OF THE INVENTION

Figure 1:
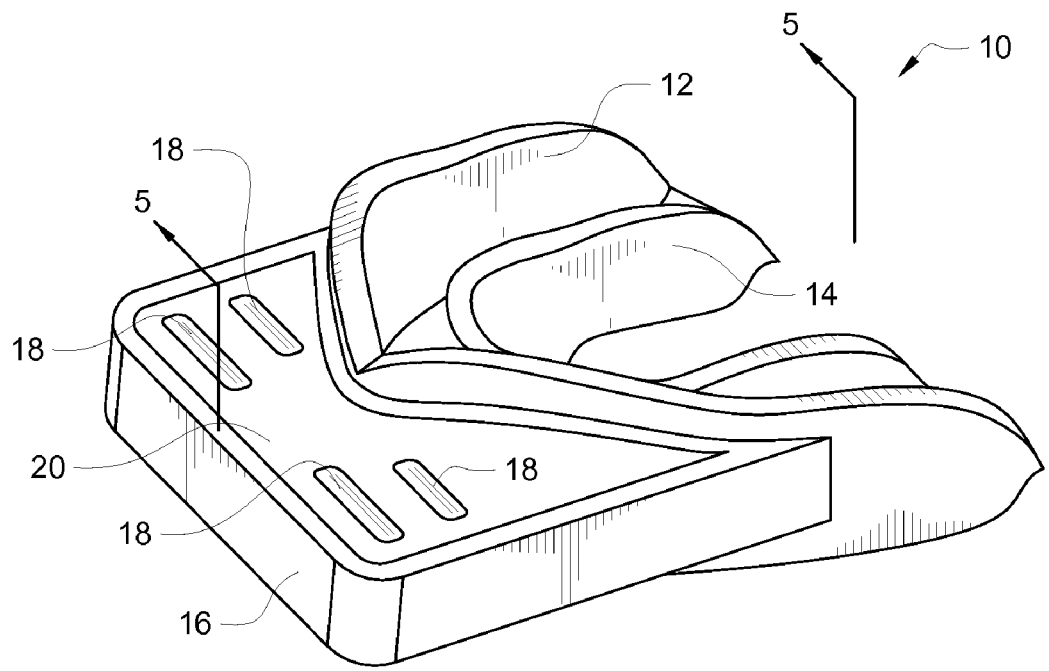
FIG. 1 illustrates an isometric view of a mouthpiece of the present invention.

Reference will now be made in detail to the presently preferred embodiments of the invention, examples of which are illustrated in the accompanying drawings. Throughout the following detailed description, the same reference numerals refer to the same elements in all figures.

Figure 2:
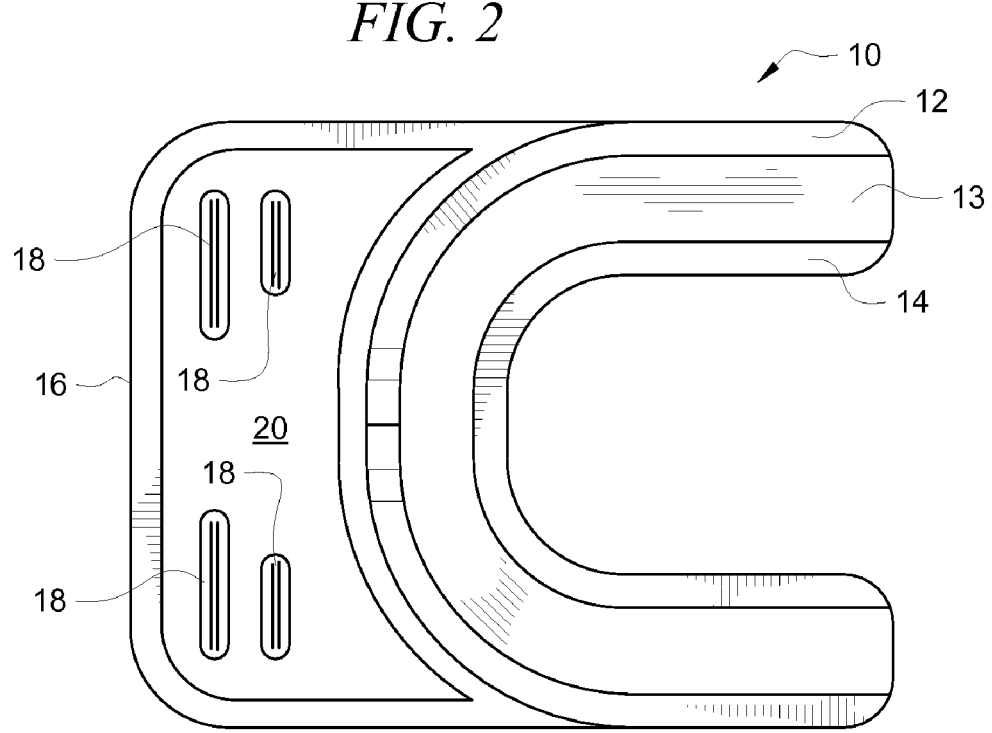
FIG. 2 illustrates a top schematic view of the present invention.

Referring to FIGS. 1 and 2, a mouthpiece of the present invention will be described. The body of the mouthpiece 10 is similar to many mouthpieces, including that described in U.S. Pat. No. D539,429. The body of the mouthpiece 10 has a front top wall 12 and a back top wall 14 (the lower walls of some embodiments are visible in FIG. 5) forming an upper trough 13 for accepting the upper teeth of a user. The front top wall 12 is placed between the upper lip of the user and the upper teeth of the user.

A heat retention mass 20 is disposed in the front surface of the mouthpiece 10 and in some embodiments; the heat retention mass 20 is contained within an encapsulation 16 protecting the heat retention mass 20. In some embodiments, vents 18 are provided to allow heat to enter through the encapsulation 16 and/or to provide a textured grip for inserting and removing the mouthpiece 10 from the user's mouth.

There are several uses for heating the mouthpiece 10, though the mouthpiece 10 of the present invention is in no way limited to these applications. One use is for applying an oral compound such as teeth whitener. By pre-heating the heat retention mass 20, some teeth whiteners perform better or faster. Additionally, the heat provides comfort to the user. Another use for the mouthpiece 10 of the present invention is where the oral compound is for making dental impressions. Often the compound used to take an impression is cold and, due to the length of time required for this compound to set, the cold feeling provides discomfort to the user. By pre-heating the heat retention mass 20, the mouthpiece 10 is subsequently heated by conduction and, therefore, the compound is later heated by conduction. Not only will the compound feel more comfortable to the user, but the heat will decrease the time required for the compound to set.

Figure 3:
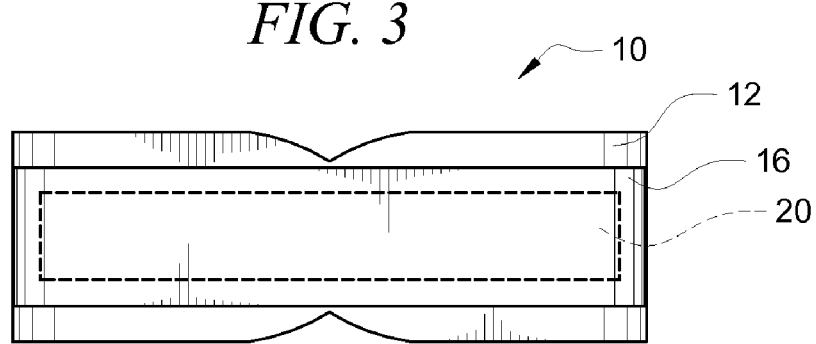
FIG. 3 illustrates a front view of the present invention.

Referring to FIG. 3, a front view of the present invention will be described. THE heat retention mass 20 is disposed in the front surface of the mouthpiece 10 and in some embodiments; the heat retention mass 20 is contained within an encapsulation 16 protecting the heat retention mass 20.

Figure 4:
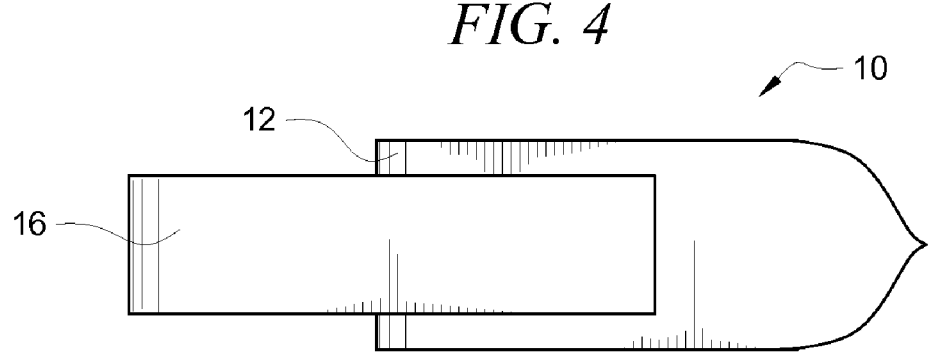
FIG. 4 illustrates a side view of the present invention.

Referring to FIG. 4, a side view of the present invention will be described. Although the heat retention mass 20 is not limited to any particular size, in the example shown, the heat retention mass 20 and its optional protective cover 16 is slightly shorter than the outside wall 12 and extends outwardly away from the user's mouth.

Figure 5:
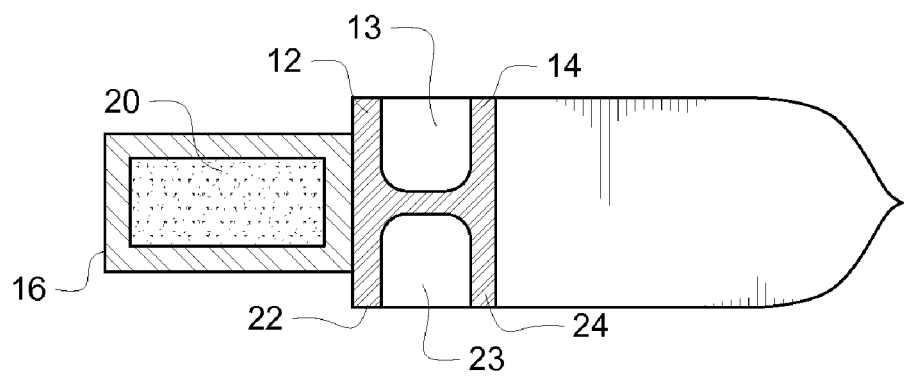
FIG. 5 illustrates a cross sectional view of the present invention along line 5-5 of FIG. 1.

FIG. 5, a side cross-sectional view of the present invention will be described. In this view, the heat retention mass 20 is shown surrounded by a protective cover or coating 16. The body of the mouthpiece 10 has a mouthpiece section with a front top wall 12 and a back top wall 14 forming an upper trough 13 for accepting the upper teeth of a user. The front top wall 12 is placed between the upper lip of the user and the upper teeth of the user. The mouthpiece section also has a front lower wall 22 and a back lower wall 24 forming a lower trough 23 for accepting the lower teeth of a user. The front lower wall 22 is placed between the upper lip of the user and the upper teeth of the user.

The heat retention mass 20 is made from any suitable material that is capable of being heated while outside of the user's mouth and retaining at least some of the heat for distribution after insertion into the user's mouth. In one embodiment, the material is rock and more specifically, lava rock. In other embodiments, the material includes metals such as steel, iron, copper, etc. Being made of such materials, heating of the mouthpiece 10 is accomplished by placing the mouthpiece 10 in a warm environment (e.g., hot water, boiling water, oven) until it accepts sufficient heat. In embodiments with this class of material, the mouthpiece 10 is not suitable for heating in a microwave oven. In still other embodiments, the heat retention mass 20 is a liquid such as water or a gel and to heat the mouthpiece 10, either the mouthpiece 10 is placed in a warm environment (e.g., hot water, boiling water, oven) or the mouthpiece 10 is heated in a microwave oven.

Equivalent elements can be substituted for the ones set forth above such that they perform in substantially the same manner in substantially the same way for achieving substantially the same result.

It is believed that the system and method of the present invention and many of its attendant advantages will be understood by the foregoing description. It is also believed that it will be apparent that various changes may be made in the form, construction and arrangement of the components thereof without departing from the scope and spirit of the invention or without sacrificing all of its material advantages. The form herein before described being merely exemplary and explanatory embodiment thereof. It is the intention of the following claims to encompass and include such changes.

What is claimed is:

1. A heated mouthpiece comprising:
a mouthpiece section having a front top wall and a back top wall forming an upper trough, the front top wall placed between an upper lip of a user and upper teeth of the user; and
a heat retention mass comprising lava rock disposed on a front surface of the mouthpiece section, the heat retention mass in thermal contact with the mouthpiece section, the heat retention mass affixed to a front surface of the mouthpiece section, the entire heat retention mass extending outwardly from the front surface of the mouthpiece section in front of front teeth of the user when the mouthpiece section is disposed within the user's mouth, the heat retention mass is heated outside of the mouth of the user and the heat retention mass conducts stored heat to the mouthpiece section while the mouthpiece section is within the mouth of the user;
wherein the heat retention mass is mounted to the mouthpiece section at a location that extends outward of the mouth, the entire heat retention mass positioned forward of the user's front teeth when the mouthpiece section is inserted into the user's mouth.

2. The heated mouthpiece of claim 1, wherein the heat retention mass is encapsulated within a continuation of the mouthpiece section and the entire heat retention mass is located in front of front teeth of the user when the heated mouthpiece is inserted into the mouth of the user.

3. The heated mouthpiece of claim 1, wherein the mouthpiece section further comprises a front lower wall and a back lower wall forming an lower trough.

4. A method of using a heated mouthpiece comprising:
providing a heated mouthpiece, the heated mouthpiece comprising:
a mouthpiece section having a front top wall and a back top wall forming an upper trough, the front top wall placed between an upper lip of a user and upper teeth of the user;
a heat retention mass comprising lava rock disposed on a front surface of the mouthpiece section, the entire heat retention mass extending outwardly from the front top wall, the heat retention mass being substantially in front when the mouthpiece section is disposed within the user's mouth, the heat retention mass made of a solid material, the heat retention mass in direct thermal contact with the mouthpiece section and heat provided to the heat retention mass before the heat retention mass is inserted into the mouth is stored in the heat retention mass until the heat is conducted to the mouthpiece section while the mouthpiece section is within the mouth;
wherein the heat retention mass is mounted to the mouthpiece section at a location that extends outward of the user's mouth, the entire heat retention mass positioned forward of the user's front teeth when the mouthpiece section is inserted into the user's mouth;
heating the heat retention mass;
placing an oral compound in the upper trough;
placing an oral compound in the lower trough; and
inserting the mouthpiece section into the mouth with the upper teeth in the upper trough and the lower teeth in the lower trough whereas heat from the heat retention mass subsequently transfers to the mouthpiece section and subsequently to the oral compound, thereby heating the oral compound.

5. The method of claim 4, wherein the heat retention mass is heated in hot water.

6. The method of claim 4, wherein the heat retention mass is heated in a microwave oven.

7. The method of claim 4, wherein the heat retention mass is encapsulated within a continuation of the mouthpiece section.

8. A heated mouthpiece comprising:
a mouthpiece section comprising a front wall connected to a back wall forming a trough, the trough sized to accept and surround the upper teeth of a user; and
a heat retention mass made of lava rock and interfaced to a front surface of the front wall and extending outwardly away from the front wall, the heat retention mass extending such that the entire heat retention mass extends from the front surface through the lips and outside of a mouth of the user when the upper teeth are in the trough, the heat retention mass in thermal contact with the mouthpiece section, external heat provided to the heat retention mass before the mouthpiece is inserted into a the mouth of the user and the heat conducts from the heat retention mass to the mouthpiece section after insertion;

wherein the heat retention mass is mounted to the mouthpiece section at a location that extends outward of the user's mouth, the entire heat retention mass positioned forward of the user's front teeth when the mouthpiece section is inserted into the user's mouth.

9. The heated mouthpiece of claim 8, wherein the heat retention mass is encapsulated within a continuation of the mouthpiece section and the entire heat retention mass is located in front of front teeth of the user when the heated mouthpiece is inserted into the mouth of the user.

10. The heated mouthpiece of claim 8, wherein the mouthpiece section further includes a lower trough for surrounding a plurality of lower teeth of the mouth.

* * * * *